United States Patent
Pauly

(10) Patent No.: US 9,329,300 B2
(45) Date of Patent: *May 3, 2016

(54) DEPTH DETERMINATION IN X-RAY BACKSCATTER SYSTEM USING FREQUENCY MODULATED X-RAY BEAM

(71) Applicant: Nucsafe, Inc., Oak Ridge, TN (US)

(72) Inventor: Steven W. Pauly, Knoxville, TN (US)

(73) Assignee: NUCSAFE, INC., Oak Ridge, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/932,942

(22) Filed: Nov. 4, 2015

(65) Prior Publication Data

US 2016/0070021 A1   Mar. 10, 2016

Related U.S. Application Data

(63) Continuation-in-part of application No. 14/108,571, filed on Dec. 17, 2013, now Pat. No. 9,201,028.

(51) Int. Cl.
*G01N 23/203*   (2006.01)
*G01V 5/00*   (2006.01)

(52) U.S. Cl.
CPC ............ *G01V 5/0025* (2013.01); *G01N 23/203* (2013.01); *G01N 2223/053* (2013.01); *G01N 2223/345* (2013.01)

(58) Field of Classification Search
CPC .......... G01N 23/20066; G01N 23/203; G01N 2223/053; G01N 23/063; G01N 23/304; G01N 23/345; G01N 23/41
See application file for complete search history.

(56) References Cited

U.S. PATENT DOCUMENTS

| | | | | |
|---|---|---|---|---|
| 5,044,006 A | * | 8/1991 | Cyrulnik | A61N 5/10 378/113 |
| 7,151,818 B1 | * | 12/2006 | Hanington | H05G 1/10 378/104 |
| 7,440,542 B2 | * | 10/2008 | Baumann | A61B 6/484 378/44 |
| 8,111,808 B1 | * | 2/2012 | Wood | G01N 24/084 378/62 |
| 8,411,820 B1 | * | 4/2013 | Browder | G01N 24/084 378/43 |
| 8,411,821 B1 | * | 4/2013 | Wood | G01N 24/084 378/43 |
| 8,433,037 B1 | * | 4/2013 | Wood | G01V 5/0025 378/57 |
| 8,983,034 B2 | * | 3/2015 | Wood | G01N 23/203 378/57 |
| 9,213,006 B2 | * | 12/2015 | Wood | G01N 23/203 |
| 2012/0141009 A1 | * | 6/2012 | Wood | G01N 24/084 382/132 |
| 2014/0355741 A1 | * | 12/2014 | Wood | G01N 23/20008 378/86 |
| 2015/0168137 A1 | * | 6/2015 | Pauly | G01N 23/203 378/87 |

* cited by examiner

*Primary Examiner* — Thomas R Artman

(74) *Attorney, Agent, or Firm* — Luedeka Neely Group, P.C.

(57) ABSTRACT

An X-ray backscatter imaging system uses frequency modulated X-rays to determine depth of features within a target. An X-ray source generates X-ray radiation modulated by a frequency-modulated bias current. The X-ray radiation impinges upon and is backscattered from multiple depths within the target. A scintillating material receives the backscattered X-rays and generates corresponding photons. A photodetector, having gain modulated by the frequency modulation signal from the local oscillator, receives the photons from the scintillating material and generates an analog output signal containing phase delay information indicative of the distance travelled by the X-rays backscattered from multiple depths within the target. The analog output signal is sampled by an analog-to-digital converter to create a digital output signal. A computer processor performs a discrete Fourier transform on the digital output signal to provide target depth information based on the phase delay information.

15 Claims, 8 Drawing Sheets

DEPTH DETERMINATION IN X-RAY BACKSCATTER SYSTEM USING FREQUENCY MODULATED X-RAY BEAM

RELATED APPLICATIONS

This application is a continuation-in-part of and claims priority to co-pending U.S. patent application Ser. No. 14/108,571, titled "Depth Determination in X-ray Backscatter System Using Frequency Modulated X-ray Beam," filed Dec. 17, 2013.

FIELD

This invention relates to the field of X-ray imaging. More particularly, this invention relates to a system for determining depth information in an X-ray backscatter imaging system.

BACKGROUND

X-ray backscatter systems can be used to perform non-destructive testing (NDT) for a variety of materials and applications. One important benefit of an X-ray backscatter system is that it requires access to only one side of the object under test. In a typical X-ray backscatter system, an X-ray generator is operated continuously at a fixed frequency and the resulting X-rays are highly collimated to form a beam that is directed on the target. As this beam is scanned over the target, X-rays penetrate the target and interact with the materials of the target and scatter in various directions. A detector suitable for detecting the scattered X-rays is located near the X-ray generator and is used to detect the backscattered X-rays and produce a signal therefrom. The X-ray backscatter system records the backscattered signal for each position of the X-ray beam on the target during a scan and thereby forms a pixel for each position. The resulting scan of the target is a collection of pixels that contain the X-ray backscattered intensity for each pixel. This collection of pixels can be displayed as an image. Typical images provide for viewing objects, defects, and structures buried within the target.

The usefulness of X-ray backscatter systems could be improved by the addition of depth information for each pixel. If the depth of the interactions were collected, or a distribution of depths for each pixel were available, it would provide a signal-to-noise ratio enhancement of the image by allowing only the signals from a selected depth to be viewed. This would also provide depth information for the defects or objects found within the target that could aid in remediation or further analysis.

Laser radar (LIDAR) systems that implement frequency modulation have been used to measure distances to targets located far from the LIDAR system. Since light photons generally reflect from the outer surface of the target, such systems cannot provide information regarding the depth of features within the target. Although light radiation and X-ray radiation both comprise photons, the X-ray and gamma-ray portions of the electromagnetic spectrum provide unique challenges because X-ray and gamma-ray photons cannot be easily focused and split using optical elements as in most LIDAR systems. Attempts to determine the depth of an interaction using conventional X-ray backscatter systems have involved large, costly and complex collimators, arrays of detectors, and coded apertures.

What is needed, therefore, is a method for determining the depth of interactions within a target using an X-ray backscatter system that does not require the high cost and hardware complexity of multiple detectors, collimation, and coded apertures.

SUMMARY

The above and other needs are met by an X-ray backscatter imaging system that uses frequency modulated X-rays to determine the depth of features within a target. In one preferred embodiment, the system includes a modulation signal source for generating a frequency modulation signal, a magnetic field generator for generating a magnetic field, and means for modulating the magnetic field with the frequency modulation signal to provide a frequency-modulated magnetic field. An X-ray radiation source is disposed adjacent the magnetic field generator and generates X-ray radiation modulated by the frequency-modulated magnetic field. The X-ray radiation impinges upon and penetrates a target, and is backscattered from multiple depths within the target. Scintillating material receives X-ray radiation backscattered from the multiple depths within the target and generates photons corresponding to the backscattered X-ray radiation. The system includes a bias signal source for generating a bias signal, and means for modulating the bias signal with the frequency modulation signal to provide a frequency-modulated bias signal. Photon detection means receive the photons generated by the scintillating material, receive the frequency-modulated bias signal, and generate an analog output signal based thereon. The analog output signal contains phase delay information indicative of distance travelled by the X-ray radiation backscattered from the multiple depths within the target. An analog-to-digital converter samples the analog output signal at a sampling frequency and converts the analog output signal into a digital output signal. A computer processor receives the digital output signal and performs a discrete Fourier transform on the digital output signal to provide target feature depth information based on the phase delay information.

In some embodiments, the frequency-modulated magnetic field deflects an electron beam within the X-ray radiation source, thereby modulating the X-ray radiation.

In some embodiments, the magnetic field generator comprises a magnetic coil.

In some embodiments, the means for modulating the magnetic field comprise a mixer circuit for mixing the frequency modulation signal with a voltage across the magnetic coil of the magnetic field generator.

In some embodiments, the modulation signal source comprises a voltage-controlled oscillator.

In some embodiments, the modulation signal source comprises a pulse generator and the frequency modulation signal comprises a series of pulses.

In some embodiments, the bias signal source comprises a DC bias voltage source.

In some embodiments, the scintillating material comprises polyvinyl toluene (PVT).

In some embodiments, the means for modulating the bias signal with the frequency modulation signal comprise a mixer circuit.

In some embodiments, the photon detection means comprise a photodetector selected from the group consisting of a photomultiplier tube (PMT), a silicon photomultiplier (SiPM), and an avalanche photodetector (APD).

In some embodiments, the system includes a low-pass filter having a cut-off frequency that is less than the sampling frequency. The low-pass filter receives and low-pass filters the analog output signal prior to conversion to the digital output signal.

In another preferred embodiment, the system includes electromechanical means for directly modulating the X-ray radiation based on a frequency modulation signal prior to the X-ray radiation impinging upon the target. In some embodiments, the electromechanical means comprise a chopper wheel that directly modulates the X-ray radiation based on the frequency modulation signal.

In yet another embodiment, the system includes a local oscillator for generating a frequency modulation signal, a current source for generating a bias current, and a mixer circuit for modulating the bias current with the frequency modulation signal to provide a frequency-modulated bias current. An X-ray radiation source receives the frequency-modulated bias current and generates X-ray radiation modulated by the frequency-modulated bias current. The X-ray radiation impinges upon and penetrates a target, and is backscattered from multiple depths within the target. A scintillating material receives the X-ray radiation backscattered from the multiple depths within the target and generates photons corresponding to the backscattered X-ray radiation. The system includes a bias voltage source for generating a bias voltage and a mixer circuit for modulating the bias voltage with the frequency modulation signal from the local oscillator to provide a frequency-modulated bias voltage. A photodetector receives the photons generated by the scintillating material and receives the frequency-modulated bias voltage and generates an analog output signal based thereon. The analog output signal contains phase delay information indicative of the various distances travelled by the X-rays backscattered from the various depths within the target. The analog output signal passes through a low-pass filter and is sampled by an analog-to-digital converter to create a digital output signal. A computer processor performs a discrete Fourier transform on the digital output signal to provide target feature depth information based on the phase delay information.

In another aspect, the invention provides an X-ray backscatter imaging method. Preferred embodiments of the method include the following steps, which are not necessarily performed in the order listed:

(a) generating a frequency modulation signal;
(b) generating a first bias signal;
(c) modulating the first bias signal with the frequency modulation signal to provide a first frequency-modulated bias signal;
(d) generating X-ray radiation modulated by the first frequency-modulated bias signal;
(e) directing the X-ray radiation onto a target;
(f) receiving X-ray radiation that is backscattered from multiple depths within the target;
(g) generating photons in a scintillating material that correspond to the X-rays backscattered from multiple depths within the target;
(h) generating a second bias signal;
(i) modulating the second bias signal with the frequency modulation signal to provide a second frequency-modulated bias signal;
(j) detecting the photons generated by the scintillating material;
(k) generating an analog output signal based on the detected photons and the second frequency-modulated bias signal, where the analog output signal contains phase delay information indicative of the various distances travelled by the X-rays backscattered from the various depths within the target;
(l) converting the analog output signal to a digital output signal; and
(m) performing a discrete Fourier transform on the digital output signal to provide target feature depth information based on the phase delay information.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
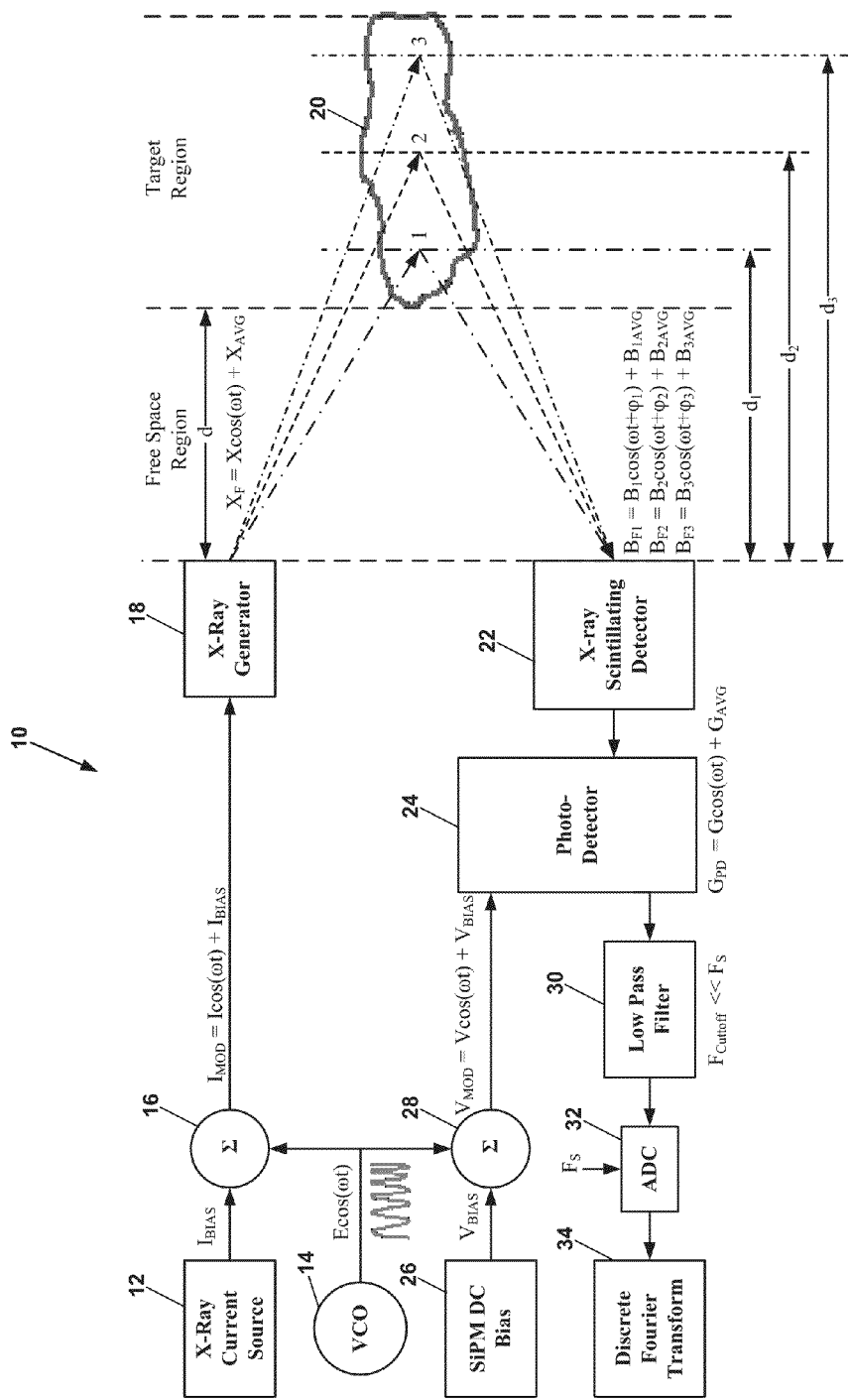
FIG. 1 depicts an X-ray backscatter system according to an embodiment of the invention.
Figure 2:
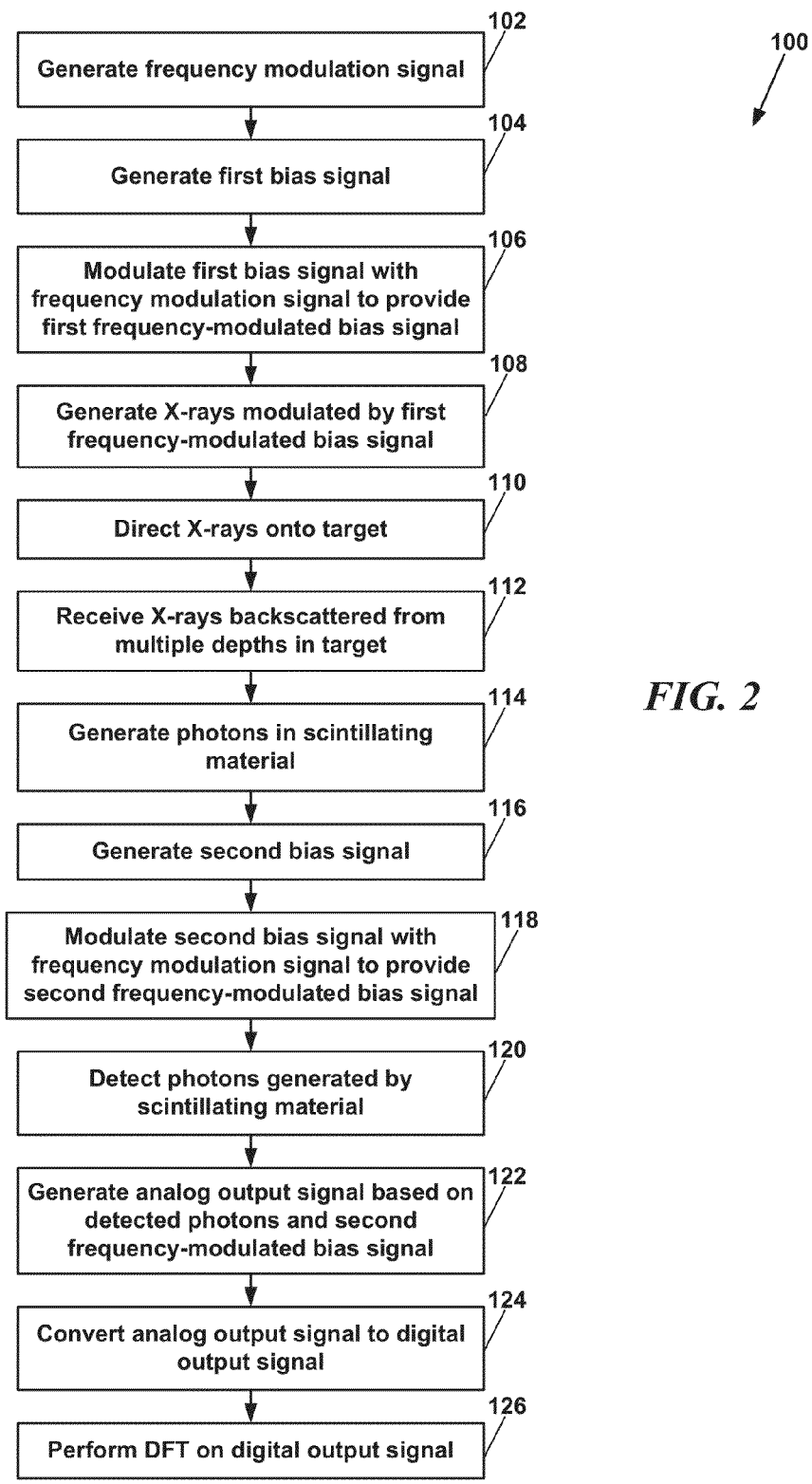
FIG. 2 depicts a method of determining target feature depth information in an X-ray backscatter system according to an embodiment of the invention.

As shown in FIGS. 1 and 2, a preferred embodiment of an X-ray backscatter imaging system 10 includes an X-ray current source 12 that generates an X-ray bias current $I_{BIAS}$ (step 104). The system includes a local oscillator (LO) 14, such as a voltage-controlled oscillator (VCO), that generates a chirp signal $E \cos(\omega t)$ (step 102), the frequency of which is linearly ramped from a starting frequency $\omega_{start}$ through an ending frequency over a sweep time $t_{sweep}$ according to:

$$\omega(t) = \omega_{start} + \frac{\Delta \omega t}{t_{sweep}}.$$

The X-ray bias current $I_{BIAS}$ is modulated by the chirp signal $E \cos(\omega t)$ in a mixer circuit 16 to produce a modulated X-ray intensity current $I_{MOD}$ (step 106) according to:

$$I_{MOD} = I \cos(\omega t) + I_{BIAS}.$$

The modulated signal may have a bandwidth of approximately 100 MHz.

The modulated X-ray intensity current $I_{MOD}$ drives an X-ray generator 18 that generates X-ray flux (step 108) expressed as:

$$X_F = X \cos(\omega t) + X_{AVG}.$$

The X-rays emitted from the generator 18 travel through free space over a stand-off distance d and impinge upon a target 20 (step 110). The X-rays backscatter from various depths within the target 20 and undergo phase delays proportional to the intensity wave propagation time, which is also proportional to the distance d to the target. FIG. 1 illustrates backscatter from depths 1, 2 and 3 within the target 20 that are at distances $d_1$, $d_2$, and $d_3$, respectively, from the generator 18. Since the X-rays interact with the target at multiple depths, the resulting backscatter signal $B_F$ contains many proportional delays corresponding to the amount of backscatter at each depth. The X-ray signals backscattered from depths 1, 2 and 3 may be expressed as:

$$B_{F1} = B_1 \cos(\omega t + \sigma_1) + B_{1AVG},$$

$$B_{F2} = B_2 \cos(\omega t + \sigma_2) + B_{2AVG}, \text{ and}$$

$$B_{F3} = B_3 \cos(\omega t + \sigma_3) + B_{3AVG}.$$

The backscattered X-ray signals are received by a gamma ray or x-ray sensitive detector 22 (step 112), which in a preferred embodiment is a scintillating material such as polyvinyl toluene (PVT). Such material emits visible light (photons) in proportion to the intensity and energy of the received X-ray or gamma ray radiation (step 114). In preferred embodiments, the position of the X-ray generator 18 is fixed with respect to the position of the scintillating detector 22 as the X-ray radiation from the generator 18 is scanned across the target 20. A photodetector 24, such as a photomultiplier tube (PMT), silicon photomultiplier (SiPM), or avalanche photodetector (APD), converts the light emitted by the scintillating detector 22 into an electrical current (step 120). The amplitude of that current is proportional to the energy of the received light for pulsed mode operation. In continuous current mode operation, the average current amplitude is proportional to the intensity of the received X-ray signal.

In a preferred embodiment, the photodetector 24 is biased by a voltage $V_{BIAS}$ to provide a gain $G_{PD}$. The bias voltage $V_{BIAS}$ is preferably generated by a DC bias voltage source 26 (step 116). The bias voltage $V_{BIAS}$ is modulated by the chirp signal E cos(ωt) from the LO 14 in a mixer circuit 28 to produce a modulated bias voltage $V_{MOD}$ (step 118) according to:

$$V_{MOD} = V \cos(\omega t) + V_{BIAS}.$$

The gain $G_{PD}$ provided by the photodetector 24 may be expressed as:

$$G_{PD} = G \cos(\omega t) + G_{AvG}.$$

Using the modulated bias voltage $V_{MOD}$, the photodetector 24 mixes the received backscattered X-ray signal with the locally generated chirp signal to generate an output signal (step 122). The output signal from the photodetector 24 passes through a low pass filter 30 and is digitized by an analog-to-digital converter (ADC) 32 at a sampling frequency $F_S$ (step 124). The resulting digital samples undergo analysis using a discrete Fourier transform (DFT) implemented in a computer processor 34 (step 126). The DFT provides depth information for features within the target as frequency information. As the X-ray radiation from the source 18 is scanned across the target 20, this process is repeated for each pixel location in the scan, thereby forming an X-ray image of the target containing feature depth information.

As described above, the backscattered X-ray photons do not interact directly with the photodetector 24. Rather, the interactions occur in the scintillator material of the scintillating detector 22 which emits visible light photons in response to the X-ray photons interacting within the scintillating material. The interaction depths within the scintillating material is random for each X-ray photon and this randomness represents a noise source in the depth determination. These random interactions in the scintillating material represent random distances being added to the true round trip distances ($d_1$, $d_2$, $d_3$) to features within the target. Thus, the true distances to the features within the target are available by time averaging of the backscattered signals ($B_{F1}$, $B_{F2}$, $B_{F3}$) for each pixel of the target image.

Figure 3:
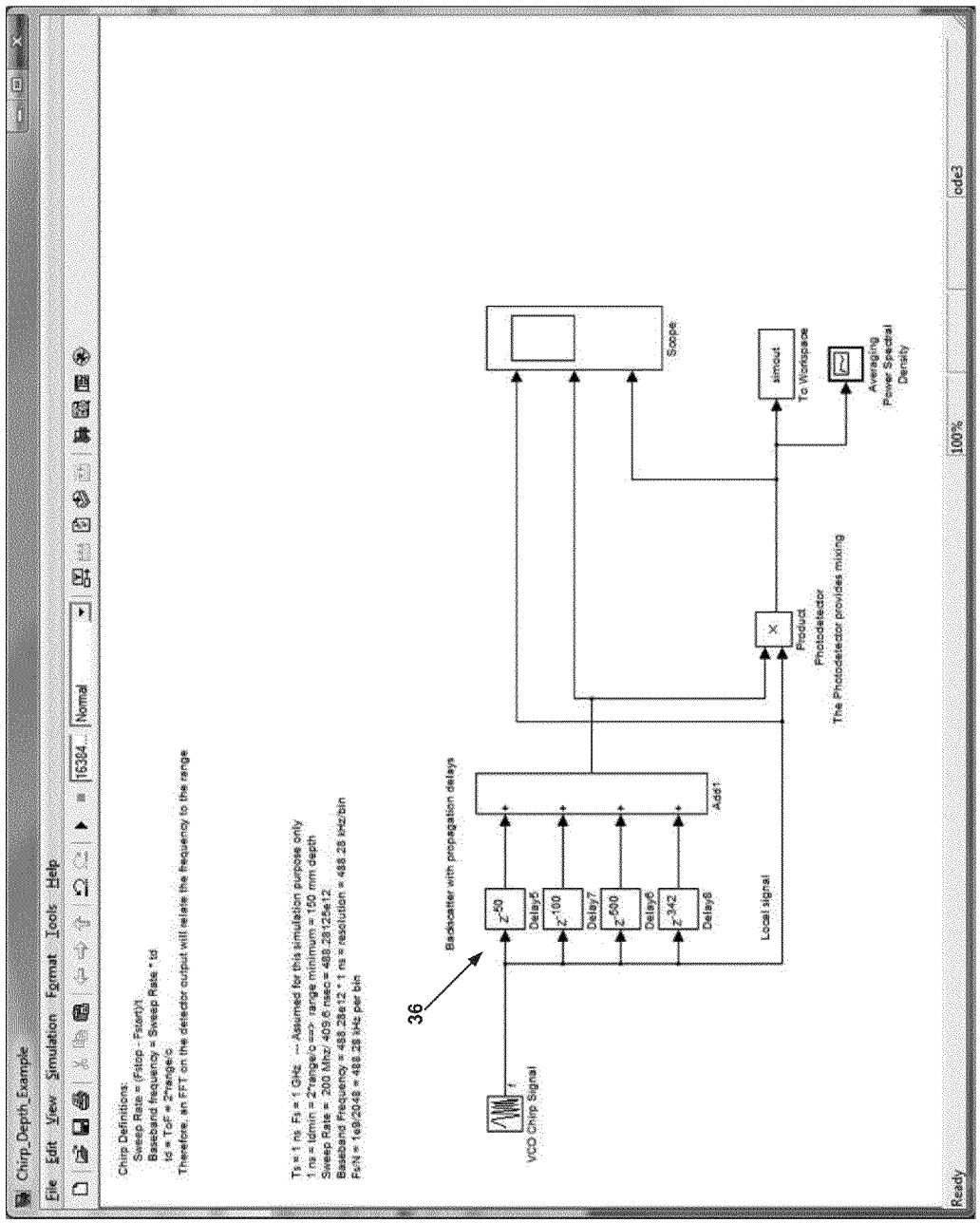
FIG. 3 depicts a first simplified simulation of the operation of an X-ray backscatter imaging system according to an embodiment of the invention.

FIG. 3 depicts a simplified simulation of the operation of an embodiment of an X-ray backscatter imaging system programmed using MATLAB® Simulink® software. For purposes of the simulation, the following parameters were used:

$$T_S = 1 \text{ nsec}, F_S = 1 \text{ GHz}$$

$$d_{MIN} = \frac{c \times T_S}{2} = \frac{(299792458 \text{ m/s}) \times (1 \text{ nsec})}{2} = 150 \text{ mm}$$

Sweep Rate =

$$\frac{F_{STOP} - F_{START}}{t} = \frac{200 \text{ Mhz}}{409.6 \text{ nsec}} = 488.28125 \times 10^{12} \text{ hz/sec}$$

$$\text{Resolution} = \frac{F_S}{\text{number of bins}} = \frac{1 \text{ GHz}}{2048} = 488.28 \text{ kHz/bin}$$

Baseband Frequency =

Figure 4:
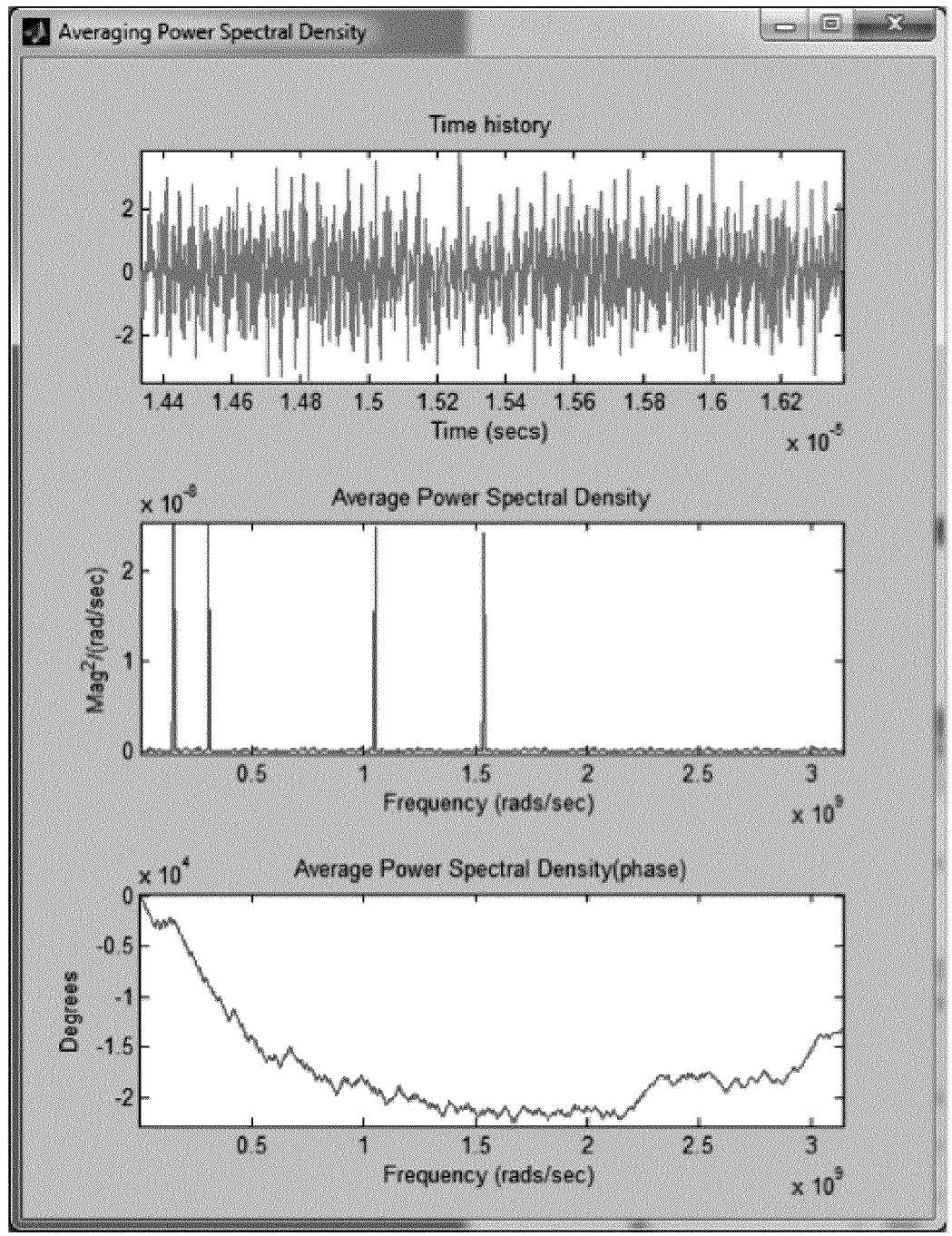
FIG. 4 depicts graphs of average power spectral density of backscattered X-ray energy as calculated by the simulation of FIG. 3.

Sweep Rate $\times T_S = 488.28125 \times 10^{12}$ hz/sec $\times 1$ nsec $= 488.28$ kHz The four different propagation delay blocks 36 in FIG. 3 simulate backscatter from four depths within a target. The center graph of FIG. 4 depicts the resulting average power spectral density in which the four amplitude spikes indicate the frequencies associated with the four target depths.

Figure 5:
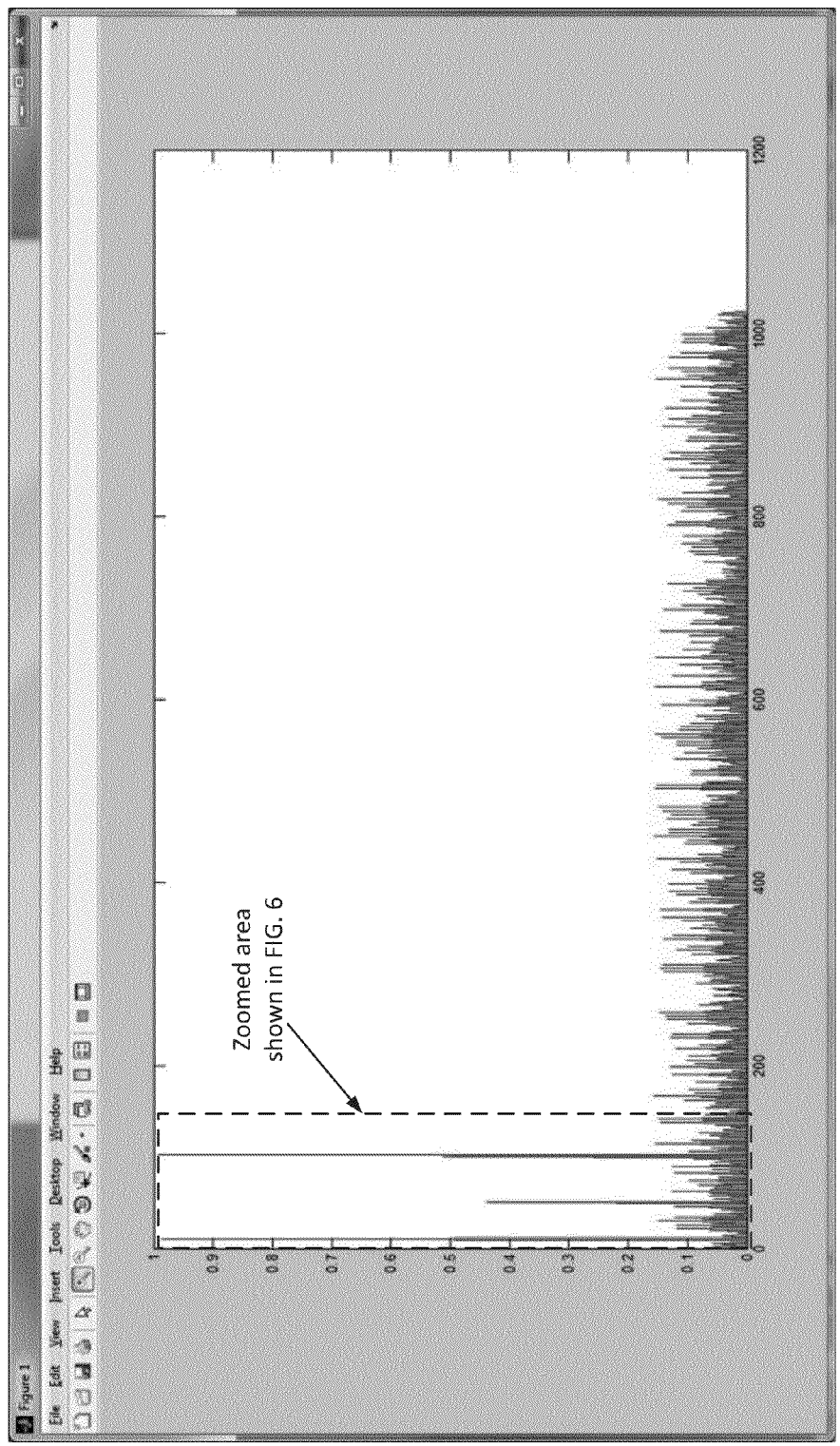
FIGS. 5 and 6 depict the results of a second simulation of the operation of an X-ray backscatter imaging system according to an embodiment of the invention.
Figure 6:
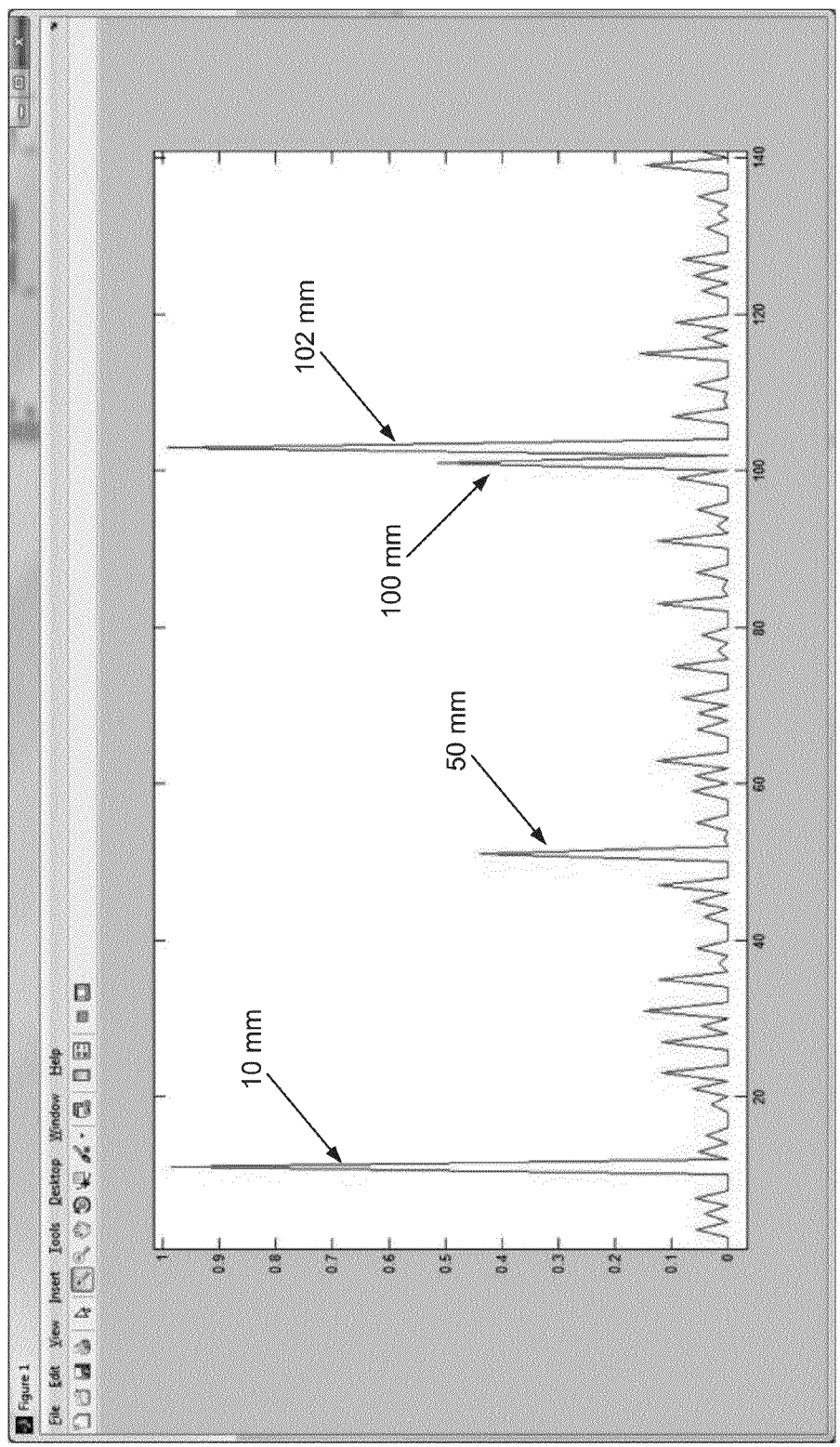

FIGS. 5 and 6 depict the results of a more general simulation performed using MATLAB®. This simulation utilized formula to determine all necessary parameters given a desired depth resolution, desired number of DFT frequency bins, and a desired chirp time. The formulae were derived to make the sample rate of the ADC equate to the chirp sweep speed. For this simulation, four different delays were applied along with attenuation for each. When provided parameters for 1 mm depth resolution (6.67 picosecond time delay per millimeter assuming the speed of light for propagation speeds), the simulation results indicate that the frequency can be swept from 0 MHz to 73.2 MHz at a sweep time of 375 nanoseconds and a sample rate of 2.67 MHz and still enable 1 mm depth determination. The resulting DFT for this simulation is depicted in FIGS. 4 and 5 where the target depths are 10 mm, 50 mm, 100 mm, and 102 mm, and the attenuation of the signal is ×1, ×0.5, ×0.5, and ×1, respectively.

In one embodiment, the X-ray generator 18 is a miniaturized high-speed modulated X-ray source (MXS), such as developed by the National Aeronautics and Space Administration (NASA). The MXS produces electrons by shining ultraviolet light from an LED onto a photocathode material, such as magnesium. The voltage driving the LED is modulated by the chirp signal E cos(ωt) from the LO 14. The electrons from the photocathode are accelerated across several kV and into a target material. Deceleration of the electrons in the target material produces X-rays modulated by the chirp signal and having characteristics determined at least in part by the target material. Some embodiments of the MXS use an electron multiplier for high X-ray production efficiency. Unlike traditional X-ray sources, the MXS does not require a heated filament in a vacuum tube which makes high-frequency modulation difficult. The MXS provides for rapid and arbitrary modulation that allows use of X-rays in time domain applications as described herein. Another low-power X-ray source is described in U.S. Pat. No. 8,081,734 B2, the entire contents of which are incorporated herein by reference.

In preferred embodiments, the modulation voltage E cos(ωt) from the LO 14 is a chirped signal, wherein the signal frequency is swept (ramped) from a start frequency to a stop frequency over a sweep period. However, other embodiments may employ other types of frequency modulation, such as using a sinusoidal frequency sweep or pulsed modulation. In embodiments using pulsed modulation, the X-ray generator 18 may be pulsed on/off, where the repetition rate of the pulses is swept from a low rate to a high rate, or visa versa, during a sweep period. The same pulsed modulation would be applied to the gain of the photodetector 24 in order to extract the phase information from the backscattered signal.

Another advantage of embodiments of the invention is the use of low-power X-ray radiation which makes the system safer to use while still obtaining images with an adequate signal-to-noise ratio. This assumes that the energy level of the backscattered X-rays is high enough for the detector 24 to operate in current mode (basically a DC level for each pixel) where the DC level varies depending on the energy level of the backscattered X-rays. In preferred embodiments, low-frequency modulation allows the X-ray generator 18 to be a relatively low-power source, and the low-frequency modulation of the backscattered X-ray signals received by the detector 24 allows for the received signals to be integrated over several modulation cycles to increase the signal-to-noise ratio.

As shown in the embodiment of FIG. 1, a single LO signal $E \cos(\omega t)$ modulates the bias current bus that drives the X-ray source 18 on the transmit side as well as the bias voltage $V_{BIAS}$ provided to the photodetector 24 on the receive side. This provides a significant advantage in terms of lower complexity and cost of components as compared to conventional optical range-finding systems and microwave communication systems that extract the LO signal to be used on the receive side from the transmit signal. The technique of using the same LO signal on both the transmit and receive sides is often called "homodyne." "Heterodyne" is a term often used to describe mixing two signals where one of the signals is purposely offset slightly in frequency from the other, and is often used in radio receivers where the LO signal used in the transmitter is not available. Embodiments of the backscatter x-ray system described herein generate the x-rays and receive them after they have travelled and interacted with the target. The "homodyne" technique of using the same LO signal to modulate both the transmitted signal and the received signal effectively highlights the phase difference impressed upon the received signal due to the distance (depth within target) that the received signal travelled. Although it may be possible to implement a heterodyne in alternative embodiments by modulating the photodetector 24 with a slightly different frequency than was used to transmit the x-rays, there is no significant benefit to be gained in exchange for the additional complexity of including a second modulation source.

Figure 7:
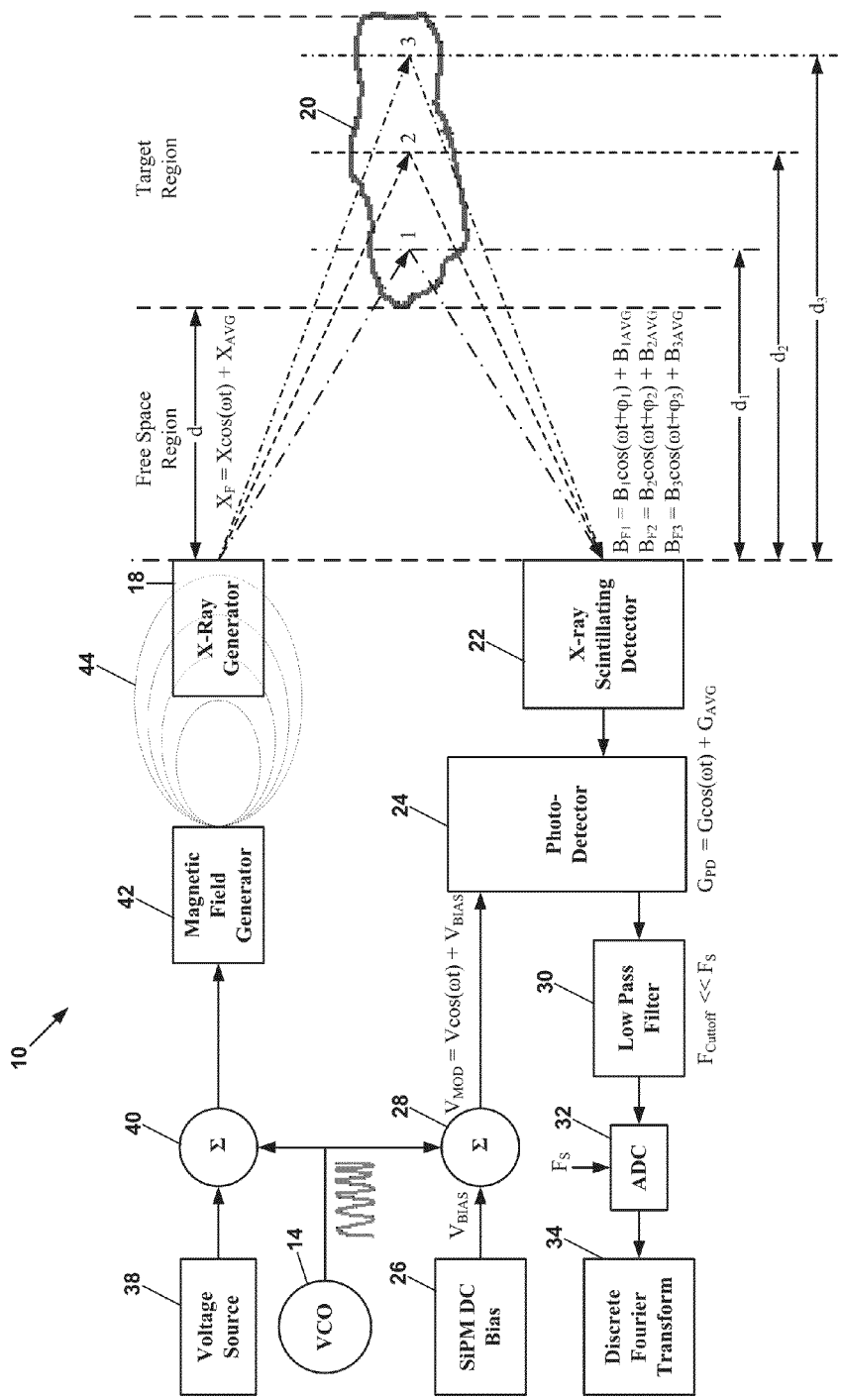
FIGS. 7 and 8 depict X-ray backscatter systems according to alternative embodiments of the invention.

FIG. 7 depicts an alternative embodiment in which a magnetic field generator 42 generates a modulated magnetic field 44 that modulates the X-ray radiation emitted from the X-ray generator 18. In this embodiment, a voltage source 38 generates a voltage that is modulated in a mixer circuit 40 by the chirp signal from the VCO 14 to produce a modulated voltage. The modulated voltage is provided across a coil in the magnetic field generator 42 to generate the modulated magnetic field 44. The modulated magnetic field 44 deflects an electron beam within the front end of the X-ray generator 18 which in turn results in a change in the intensity of the emitted X-ray radiation proportional to the changing magnetic field 44, thereby effectively modulating the X-rays produced by the generator 18.

For many years prior to the rise in popularity of LCD displays, magnetic "yokes" were used to steer and deflect electron beams at high speeds in cathode ray tube televisions and computer monitors. Embodiments of the present invention apply similar techniques to deflect an electron beam that strikes a tungsten target in an X-ray tube. One advantage to using this magnetic modulation method is that high frequency modulation is achievable, which is necessary for effective X-ray target imaging. Another advantage is that it may be possible to implement magnetic modulation to an existing X-ray generator externally without modifying the internal structure of tube, because the magnetic modulation field just needs to penetrate the enclosure of the X-ray generator.

Figure 8:
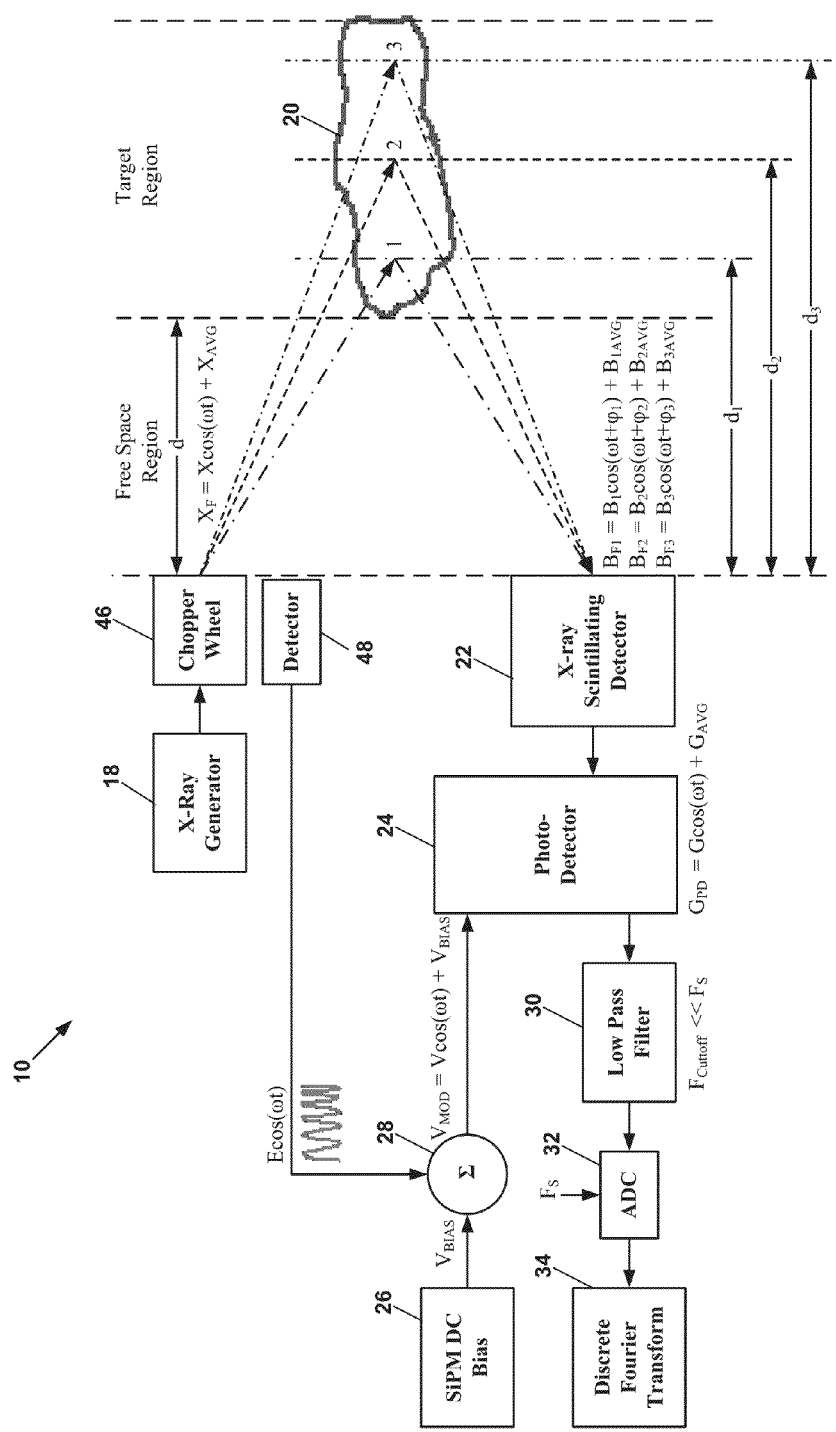

FIG. 8 depicts an alternative embodiment in which the X-ray radiation emitted from the X-ray generator 18 is mechanically or electromechanically modulated. In one version of this embodiment, the X-ray radiation is directly modulated using a chopper wheel 46. In this embodiment, the wheel 46 has a pattern of etched or laser-scribed small holes or slits of varying size across the pattern. As the wheel 46 rotates, an X-ray beam passing through the pattern would have its intensity modulated based on the geometry of the pattern and the speed of the rotating wheel. To acquire a local reference signal for recovering the target depth information, a reference detector 48 may be located so as to detect energy from the X-ray beam emitted from the wheel 46.

In another embodiment, the electromechanical motion needed to modulate the X-ray beam is provided by a microelectromechanical system (MEMS) actuator, such as are used in making very small and extremely fast motors (on the order of $10^6$ RPM). For example, U.S. Pat. No. 7,053,520 describes using a multiwall carbon nanotube (MWNT) motor having an axially-deflecting rotor plate that, when illuminated with a light beam, modulates light reflected therefrom by axial movement of the plate. A similar arrangement could be used to modulate an X-ray beam in an alternative embodiment of the present invention.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An X-ray backscatter imaging system comprising:
 a modulation signal source for generating a frequency modulation signal;
 a magnetic field generator for generating a magnetic field;
 means for modulating the magnetic field with the frequency modulation signal to provide a frequency-modulated magnetic field;
 an X-ray radiation source disposed adjacent the magnetic field generator and generating X-ray radiation modulated by the frequency-modulated magnetic field, wherein the X-ray radiation impinges upon and penetrates a target, and is backscattered from multiple depths within the target;
 scintillating material for receiving X-ray radiation backscattered from the multiple depths within the target and for generating photons corresponding to the backscattered X-ray radiation;

a bias signal source for generating a bias signal;

means for modulating the bias signal with the frequency modulation signal to provide a frequency-modulated bias signal;

photon detection means for receiving the photons generated by the scintillating material, receiving the frequency-modulated bias signal, and generating an analog output signal based thereon, wherein the analog output signal contains phase delay information indicative of distance travelled by the X-ray radiation backscattered from the multiple depths within the target;

an analog-to-digital converter for sampling the analog output signal at a sampling frequency and converting the analog output signal to a digital output signal; and a computer processor for receiving the digital output signal and performing a discrete Fourier transform on the digital output signal to provide target feature depth information based on the phase delay information.

2. The system of claim 1 wherein the means for modulating the magnetic field comprise a mixer circuit for mixing the frequency modulation signal with a voltage across a magnetic coil of the magnetic field generator.

3. The system of claim 1 wherein the magnetic field generator comprises a magnetic coil.

4. The system of claim 1 wherein the frequency-modulated magnetic field deflects an electron beam within the X-ray radiation source, thereby modulating the X-ray radiation.

5. The system of claim 1 wherein the modulation signal source comprises a voltage-controlled oscillator.

6. The system of claim 1 wherein the modulation signal source comprises a pulse generator and the frequency modulation signal comprises a series of pulses.

7. The system of claim 1 wherein the bias signal source comprises a DC bias voltage source.

8. The system of claim 1 wherein the scintillating material comprises polyvinyl toluene (PVT).

9. The system of claim 1 wherein the means for modulating the bias signal with the frequency modulation signal comprise a mixer circuit.

10. The system of claim 1 wherein the photon detection means comprise a photodetector selected from the group consisting of a photomultiplier tube (PMT), a silicon photomultiplier (SiPM), and an avalanche photodetector (APD).

11. The system of claim 1 further comprising a low-pass filter having a cut-off frequency that is less than the sampling frequency, the low-pass filter for receiving and low-pass filtering the analog output signal prior to conversion to the digital output signal.

12. An X-ray backscatter imaging system comprising:

an X-ray radiation source for generating X-ray radiation that impinges upon and penetrates a target, and is backscattered from multiple depths within the target;

a modulation signal source for generating a frequency modulation signal;

electromechanical means for modulating the X-ray radiation based on the frequency modulation signal prior to the X-ray radiation impinging upon the target;

scintillating material for receiving X-ray radiation backscattered from the multiple depths within the target and for generating photons corresponding to the backscattered X-ray radiation;

a bias signal source for generating a bias signal;

means for modulating the bias signal with the frequency modulation signal to provide a frequency-modulated bias signal;

photon detection means for receiving the photons generated by the scintillating material, receiving the frequency-modulated bias signal, and generating an analog output signal based thereon, wherein the analog output signal contains phase delay information indicative of distance travelled by the X-ray radiation backscattered from the multiple depths within the target;

an analog-to-digital converter for sampling the analog output signal at a sampling frequency and converting the analog output signal to a digital output signal; and a computer processor for receiving the digital output signal and performing a discrete Fourier transform on the digital output signal to provide target feature depth information based on the phase delay information.

13. The X-ray backscatter imaging system of claim 12 wherein the electromechanical means for modulating the X-ray radiation includes a micro-electromechanical system (MEMS) actuator.

14. The X-ray backscatter imaging system of claim 12 wherein the electromechanical means for modulating the X-ray radiation includes a chopper wheel.

15. An X-ray backscatter imaging system comprising:

an X-ray radiation source for generating X-ray radiation that impinges upon and penetrates a target, and is backscattered from multiple depths within the target;

a chopper wheel for modulating the X-ray radiation based on a frequency modulation signal prior to the X-ray radiation impinging upon the target;

scintillating material for receiving X-ray radiation backscattered from the multiple depths within the target and for generating photons corresponding to the backscattered X-ray radiation;

a bias signal source for generating a bias signal;

means for modulating the bias signal with the frequency modulation signal to provide a frequency-modulated bias signal;

photon detection means for receiving the photons generated by the scintillating material, receiving the frequency-modulated bias signal, and generating an analog output signal based thereon, wherein the analog output signal contains phase delay information indicative of distance travelled by the X-ray radiation backscattered from the multiple depths within the target;

an analog-to-digital converter for sampling the analog output signal at a sampling frequency and converting the analog output signal to a digital output signal; and a computer processor for receiving the digital output signal and performing a discrete Fourier transform on the digital output signal to provide target feature depth information based on the phase delay information.

* * * * *